US008440240B2

(12) United States Patent
Gao et al.

(10) Patent No.: US 8,440,240 B2
(45) Date of Patent: *May 14, 2013

(54) METHOD FOR TREATING OCULAR DEMODEX

(75) Inventors: Ying-Ying Gao, Fujan (CN); Scheffer C. G. Tseng, Pinecrest, FL (US)

(73) Assignee: TissueTech, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/181,767

(22) Filed: Jul. 13, 2011

(65) Prior Publication Data

US 2012/0004320 A1 Jan. 5, 2012

Related U.S. Application Data

(62) Division of application No. 11/911,956, filed as application No. PCT/US2006/016601 on Apr. 28, 2006, now abandoned.

(60) Provisional application No. 60/676,692, filed on Apr. 30, 2005.

(30) Foreign Application Priority Data

Nov. 9, 2006 (WO) .................. WO 2006/119174

(51) Int. Cl.
*A61K 36/00* (2006.01)

(52) U.S. Cl.
USPC ........................................ 424/725; 514/724

(58) Field of Classification Search ................... None
See application file for complete search history.

(56) References Cited

U.S. PATENT DOCUMENTS

| | | | |
|---|---|---|---|
| 4,215,113 A * | 7/1980 | Eriksson et al. ............ 514/120 |
| 4,745,100 A | 5/1988 | Gilbard et al. |
| 4,900,753 A | 2/1990 | Sutherland et al. |
| 5,208,257 A * | 5/1993 | Kabara ..................... 514/552 |
| 5,444,043 A * | 8/1995 | Fenical et al. ............. 514/18.7 |
| 5,888,984 A | 3/1999 | Brown |
| 6,022,529 A * | 2/2000 | Rock et al. ................. 424/59 |
| 6,197,305 B1 | 3/2001 | Friedman et al. |
| 6,541,042 B1 | 4/2003 | Frater-Schroder et al. |
| 6,649,660 B2 * | 11/2003 | Ninkov ..................... 514/731 |
| 2001/0051184 A1* | 12/2001 | Heng ....................... 424/461 |
| 2003/0040504 A1* | 2/2003 | Gans et al. ................. 514/72 |
| 2004/0197364 A1 | 10/2004 | Brown |
| 2004/0235742 A1 | 11/2004 | Mita et al. |
| 2004/0254165 A1* | 12/2004 | Soumyanath et al. ... 514/217.11 |
| 2005/0008714 A1 | 1/2005 | Enan |
| 2006/0068044 A1* | 3/2006 | Reynolds ................... 424/769 |
| 2006/0147408 A1 | 7/2006 | Reitz |
| 2006/0188492 A1 | 8/2006 | Richardson et al. |
| 2007/0003590 A1* | 1/2007 | Warburton ................. 424/423 |
| 2007/0020304 A1* | 1/2007 | Tamarkin et al. .......... 424/405 |
| 2010/0011989 A1 | 1/2010 | Arita et al. |

FOREIGN PATENT DOCUMENTS

| DE | 19824681 A1 | 12/1999 |
| GB | 2362574 * | 11/2001 |
| WO | WO-2001-12225 | 2/2001 |
| WO | WO 2006-119174 A1 | 11/2006 |

OTHER PUBLICATIONS

Walton et aol. Arch. Dermatol. 2004. vol. 140, pp. 563-566.*
U.S. Appl. No. 11/846,961, Filed Aug. 29, 2007, Gao
Brenan, J.A. et al., "Evaluation of patch testing in patients with chronic vulvar symptoms," Australas. J. Dermatol. 37:40-43 (1996).
Brophy, J.J., "Gas Chromatographic Quality Control for Oil of Melaleuca Terpinen-4-ol Type (Australian Tea Tree)," J. Agric. Food Chem. 37:1330-1335 (1989).
English, F.P. And Nutting, W.B., "Demodicosis of ophthalmic concern," Am. J. Ophthalmol. 91:362-372 (1981).
EP 08798898.6 Search Report mailed Feb. 1, 2011.
Ford, R.A. et al., "Monographs on fragrance raw materials," Food Chem. Toxicol. 26:407 (1988).
Gao et al., "Clinical treatment of ocular demodecosis by lid scrub with tea tree oil," Cornea 26(2):136-143 (2007).
Gao et al., "High prevalence of ocular demodex in lashes with cylindrical dandruffs and in vitro and in vivo killing studies," Inv. Ophthalmology Vis Science 46(Suppl):2655 (2005).
Gao, Y. Y. et al., "In Vitro and in Vivo killing ofd ocular Demodex by tea tree oil," Br. J. Pphthalmol. 89:1468-1473 (2005).
Gao, Y.Y. et al., "High Prevcalence of Demodex in Eyelashes with Cylindrical Dandruff," IOVS 46(9):3089-3094 (2005).
Kheirkhah et al., "Corneal Manifestations of Ocular Demodex Infestation," J Ophthalmology 143(5):743-749 (2007).
Kheirkhah, A. et al., "Fluorescin Dye Improves Microscopic Evaluation and Counting of Demodex in Blepharitis With Cylindrical Dandruff," Cornea 26(6):697-700 (2007).
Lichtenstein et al., "Insecticidal and Synergistic Components Isolated from Dill Plants," J. Agr. Food Chem (1974), vol. 22, No. 4, pp. 658-664.
Mills, C. et al., "Inhibition of acetylcholinesterase by Tea Tree oil," J. Pharm. Pharmacol. 56:375-379 (2004).
Mondello, F. et al., "In vivo activity of terpenin-4-ol, the main bioactive component of Melaleuca alternifolia Cheel (tea tree) oil against azole-susceptible and —resistant human pathogenic Candida species," BMC Infectious Diseases 6:158 (2006).
Norn, M.S., "Demodex folliculorum. Incidence and possible pathogenic role in the human eyelid," Acta Ophthalmol. Suppl. 108:7-85 (1970).
Simpson, E.L. et al., "Prevalence of botanical extract allergy in patients with contact dermatitis," Dermatitis 15:67-72 (2004).
Traina et al., "In vitro acaricidal activity of four monoterpenes and solvents against Otodectes cynotis (Acari: Psoroptidae)," Exp. Appl. Acarology 37:141-146 (2005).

* cited by examiner

Primary Examiner — Christopher R. Tate
(74) Attorney, Agent, or Firm — Wilson, Sonsini, Goodrich & Rosati

(57) ABSTRACT

The present invention relates to a method for treating a disorder chosen from ocular *Demodex*, *Demodex*-induced blepharitis, rosacea, acne, and meibomian gland dysfunction in a patient in need thereof, comprising administering to the patient a composition comprising a therapeutically effective amount of a substance chosen from at least one of an isoprenoidal essential oil such as Tea Tree Oil; Terpinen-4-ol; Carvone; alpha-Terpineol; Cardinene; d-Carvone; l-Carvone; gamma-Terpinene; alpha-Terpinene; 1,8-Cineole; alpha-Terpineol; para-Cimene; alpha-Pinene; Limonene; (R)-(+)-Limonene; alpha-Thugene; Eucalyptol; (+)-Ledene; Cuminic Aldehyde; and Myrcene; the administration comprising contacting or scrubbing an affected area of skin or hair, or eyelid margin and lashes of the patient with the composition; also disclosed are a method for treating mange and mite infestations on a mammalian animal; and kits for in-office and at home treatments of the disorders.

12 Claims, 8 Drawing Sheets

  
Fig. 4A　　Fig. 4B　　Fig. 4C
 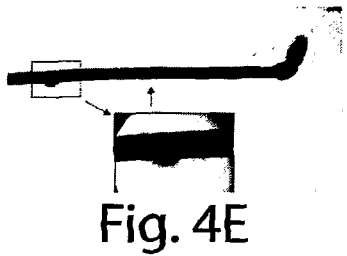
Fig. 4D　　　　　Fig. 4E
 
Fig. 4F　　　　　Fig. 4G

 
Fig. 6A　　　　Fig. 6B
 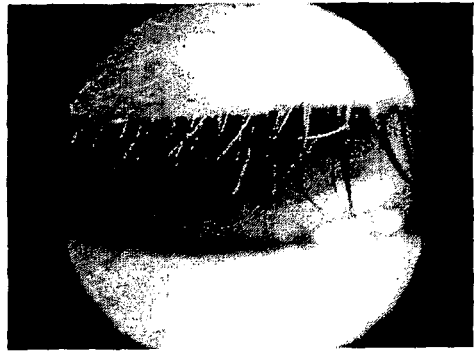
Fig. 6C　　　　Fig. 6D

METHOD FOR TREATING OCULAR DEMODEX

RELATED APPLICATION

This application is a division of U.S. patent application Ser. No. 11/911,956, filed Jul. 23, 2008, now abandoned which is a national stage entry of PCT Patent Application No. PCT/US06/16601, filed Apr. 28, 2006, which claims priority from U.S. Provisional Application No. 60/676,692, filed Apr. 30, 2005, all of which are incorporated herein by reference in their entirety.

BACKGROUND OF THE INVENTION

Blepharitis, an inflammation of the edge of the eyelid, is a common clinical problem. Blepharitis occurs as an ulcerous (staph) form or nonulcerous (seborrheic) form, or as a combination of both forms. Mixed blepharitis is seborrheic with associated staph. Patients who suffer from blepharitis as a result of an ocular *demodex* infestation often present with a number of symptoms such as a foreign body sensation, redness and itching. The symptoms can become severe enough that the patient may require surgery to achieve relief. However, even invasive treatments such as surgery often result in no significant improvement, and/or a recurrence of the *demodex* infestation.

*Demodex* mites, Class Arachnid and Order Acarina, are elongated ectoparasites. Among a wide range of reported species, only two, *demodex folliculorum* (*D. folliculorum*) and *demodex brevis* (*D. brevis*), are found on the human body surface. Adult *D. folliculorum* is commonly found in small hair follicles. *D. brevis* burrows deeper into the eyelash sebaceous gland and the meibomian gland. Both *demodex* species often coexist at the same skin area and tend to gather in the face, cheeks, the forehead, the nose, and the external ear tract, where active sebum excretion favors their habitat and breeding.

Acarine arachnids such as the *demodex* mite, *demodex folliculorum*, also can infest mammalian quadrupeds, in particular domestic animals, especially dogs, causing demodetic mange. The *demodex* mite burrows into hair follicles and sebaceous glands of the animal, the mite often causing severe dermatitis, infection, and discomfort. Demodetic mange, particularly in dogs, presents a difficult clinical problem for veterinarians, as it can involve the face and the entire body of the animal in some cases. Existing treatments can be expensive and are not always effective, with the result that affected animals are sometimes euthanized.

Mange can also be caused by the burrowing parasitic mites *Sarcoptes*, which causes scabies, and *Chorioptes*. The *Cheyletiella* mite causes a condition known as "walking dandruff" In cats, *notoedric* mange is a burrowing mite infestation that is difficult to treat.

In general, parasitic mites such as those causing mange are transmissible to humans.

Generally, *demodex* is currently treated with both systemic and topical administration of parasiticides. For example, ocular *demodex* in humans is treated by daily practice of eyelid margin scrub with diluted shampoo alone or combined with 1% mercury oxide ointment, 2% metronidazoles gel or Pilocarpine gel at the base of the eye lashes at the night time. Ophthalmic reports demonstrated a dramatic decrease in the *demodex* count observed during the follow-up examination.

However, to date, no report has demonstrated that these treatments actually kill *demodex* in vitro and no therapeutic agent has completely eradicated ocular *demodex* within one month. Indeed, recent investigations revealed that ocular *demodex* persists in 50% of patients even after one year of lid scrub with ordinary, diluted shampoo alone or combined with 1% mercury oxide ointment, 2% metronidazoles gel or Pilocarpine gel.

Rosacea is a chronic dermatological disease that affects the skin, usually the face, and sometimes the eyes. Only rarely are other parts of the upper body affected. One type of rosacea, inflammatory rosacea, causes persistent redness and pink bumps referred to as papules, and pustules on the skin. Eye inflammation also may occur, with symptoms often including sensitivity to light, blurred or otherwise impaired vision, redness, dryness, itching, burning, tearing, and the sensation of having grit or sand in the eye. The eyelids may become inflamed and swollen. "Rosacea", as the term is used herein, refers to both "rosacea of the skin" and to "ocular rosacea".

In an advanced stage of rosacea, inflammation of the eye is more apparent, and the skin thickens and becomes a deep shade of red. Rosacea is difficult to treat. Current treatments include oral antibiotics, e.g., tetracycline or doxycycline. If infections of the eyelids develop, physicians may recommend scrubbing the eyelids with diluted baby shampoo. Steroid eye drops may be prescribed in the case of severe infection.

Acne, including acne vulgaris and acne rosacea, is yet another chronic dermatological condition that is difficult to treat. Over-the-counter products for treatment of acne, including benzoyl peroxide and aluminium chlorhydroxide/sulphur can help reduce, but not cure acne. Prescription treatments, including antibiotics, retinoids, and certain hormone pills, can improve acne, but can have serious adverse effects.

Thus, a need exists for improved methods of treating ocular *demodex*, and *demodex*-induced blepharitis and rosacea. In addition, there is an ongoing need for improved treatments for the ocular condition described as meibomian gland dysfunction and for the dermatological conditions of acne and rosacea.

SUMMARY OF THE INVENTION

The present invention relates to methods and compositions for treating ocular *demodex, demodex*-induced blepharitis, meibomian gland dysfunction, acne, and rosacea.

Also disclosed are methods and compositions for treating mange and other mite infestations on a mammalian animal.

The invention inter alia includes the following, alone or in combination. In one embodiment, the invention relates to a method for treating ocular *demodex* or *demodex*-induced blepharitis in a patient in need thereof, comprising administrating to the patient a composition comprising a therapeutically effective amount of an isoprenoidal essential oil.

Another embodiment of the invention is a method for treating ocular *demodex* or *demodex*-induced blepharitis comprising administering to the patient a composition comprising a therapeutically effective amount of a substance chosen from at least one of terpinen-4-ol having the formula:

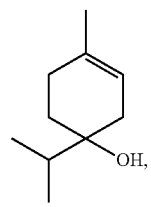

and (+)-Carvone having the formula:

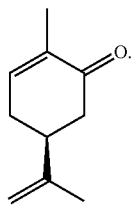

Another embodiment is a method for treating ocular *demodex* or *demodex*-induced blepharitis in a patient in need thereof, comprising administrating to the patient a composition comprising a therapeutically effective amount of a substance chosen from at least one of alpha-Terpineol, Cardinene, d-Carvone, l-Carvone, gamma-Terpinene, alpha-Terpinene, 1,8-Cineole, alpha-Terpineol, para-Cimene, alpha-Pinene, Limonene, alpha-Thugene, Eucalyptol, (+)-Ledene, Cuminic Aldehyde, and Myrcene.

Yet another embodiment of the invention is a method for treating a disorder chosen from: rosacea, acne, and meibomian gland dysfunction in a patient in need thereof, comprising: administrating to the patient a composition comprising a therapeutically effective amount of an isoprenoidal essential oil.

Another embodiment of the invention is a method for treating a disorder chosen from: rosacea, acne, and meibomian gland dysfunction in a patient in need thereof, comprising administrating to the patient a composition comprising a therapeutically effective amount of a substance chosen from at least one of: Terpinen-4-ol, having the formula:

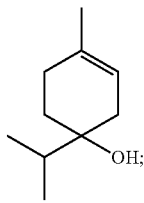

and (+)-Carvone, having the formula:

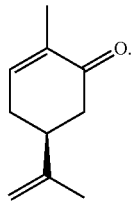

Also disclosed herein is a method for treating a disorder chosen from rosacea, acne, and meibomian gland dysfunction, in a patient in need thereof, comprising: administrating to the patient a composition comprising a therapeutically effective amount of a substance chosen from at least one of alpha-Terpineol, Cardinene, d-Carvone, l-Carvone, gamma-Terpinene, alpha-Terpinene, 1,8-Cineole, alpha-Terpineol, para-Cimene, alpha-Pinene, Limonene, alpha-Thugene, Eucalyptol, (+)-Ledene, Cuminic Aldehyde, and Myrcene.

The present invention relates, in one aspect, to a method and a kit for in-office treatment of a disorder chosen from: ocular *demodex*, ocular *demodex*-induced blepharitis, rosacea, acne and meibomian gland dysfunction, in a patient in need thereof, comprising: a therapeutically effective amount of a substance chosen from at least one of: an isoprenoidal essential oil, alpha-Terpineol, Cardinene, d-Carvone, l-Carvone, gamma-Terpinene, alpha-Terpinene, 1,8-Cineole, alpha-Terpineol, para-Cimene, alpha-Pinene, Limonene, alpha-Thugene, Eucalyptol, (+)-Ledene, Cuminic Aldehyde, Myrcene, Terpinen-4-ol having the formula:

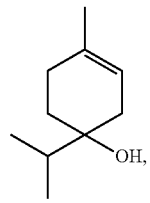

and (+)-Carvone having the formula:

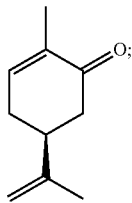

a set of directions for use of the kit for a lid scrub or other method to treat the disorder;
optionally, a plurality of disposable, sterile towels; and
optionally, a dispenser for at least one of the foregoing substances.

In another aspect, the invention relates to a kit for at-home treatment of a disorder chosen from: ocular *demodex*, ocular *demodex*-induced blepharitis, rosacea, acne, and meibomian gland dysfunction in a patient in need thereof, comprising: a therapeutically effective amount of a substance chosen from at least one of: an isoprenoidal essential oil effective to treat the disorder, Terpinen-4-ol having the formula:

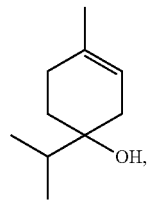

(+)-Carvone having the formula:

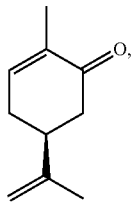

alpha-Terpineol, Cardinene, d-Carvone, l-Carvone, gamma-Terpinene, alpha-Terpinene, 1,8-Cineole, alpha-Terpineol, para-Cimene, alpha-Pinene, Limonene, alpha-Thugene, Eucalyptol, (+)-Ledene, Cuminic Aldehyde, Myrcene, and a shampoo comprising a concentration of at least one of the foregoing substances effective to treat the disorder; a set of directions for a domestic lid scrub for treating the disorder or other use of the kit to treat the disorder; optionally, a dispenser for at least one of the foregoing substances; optionally, a plurality of disposable, sterile towels; and optionally, a squeezable container for holding a facial moisturizer, the container having an opening for dispensing the moisturizer. In one embodiment, the kit includes a set of directions for mixing one of the afore-mentioned substances with a commercially available shampoo to prepare a shampoo useful for domestic lid scrub.

Yet another embodiment of the invention is a method for treating an infestation chosen from sarcoptic mange, demodectic mange, chorioptic mange, notoedric mange, and cheyletiella mite infestation on a mammalian animal, the method comprising administering to the animal in need thereof a therapeutically effective amount of a composition chosen from at least one of: an isoprenoidal essential oil, Terpinen-4-ol having the formula:

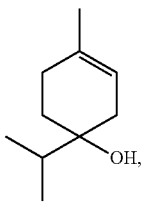

(+)-Carvone having the formula:

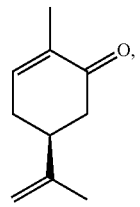

alpha-Terpineol, Cardinene, d-Carvone, l-Carvone, gamma-Terpinene, alpha-Terpinene, 1,8-Cineole, alpha-Terpineol, para-Cimene, alpha-Pinene, Limonene, alpha-Thugene, Eucalyptol, (+)-Ledene, Cuminic Aldehyde, and Myrcene.

The invention also relates to a kit for at-home or in-office treatment of a disorder chosen from sarcoptic mange, demodectic mange, chorioptic mange, notoedric mange, and cheyletiella mite infestation on a mammalian animal in need thereof, comprising: a therapeutically effective amount of a substance chosen from at least one of: an isoprenoidal essential oil effective to treat the disorder, Terpinen-4-ol having the formula:

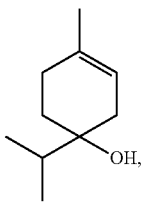

(+)-Carvone having the formula:

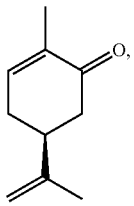

alpha-Terpineol, Cardinene, d-Carvone, l-Carvone, gamma-Terpinene, alpha-Terpinene, 1,8-Cineole, alpha-Terpineol, para-Cimene, alpha-Pinene, Limonene, alpha-Thugene, Eucalyptol, (+)-Ledene, Cuminic Aldehyde, Myrcene, and a shampoo comprising a concentration of at least one of the foregoing substances effective to treat the disorder; a set of directions for use of the kit to treat the disorder in the office or at home; optionally, a plurality of disposable, sterile towels; and optionally, a dispenser for at least one of the foregoing substances. In one embodiment, the kit includes a set of directions for mixing one of the afore-mentioned substances with a commercially available shampoo to prepare a shampoo useful for domestic scrub of the animal in need of treatment.

The present invention provides important advantages. The methods and easy-to-use kits according to various embodiments of the invention facilitate the eradication of a *demodex* infestation of the eyelids. Current methods of treating such an infestation, including lid hygiene or washing with ordinary shampoo, that is, one that does not contain an essential oil, reduces *demodex* counts but does not eradicate *demodex* infestation. Our studies have shown that a conventional treatment with daily lid scrub using Baby Shampoo could not eradicate *demodex*, possibly because ordinary shampoo has no ingredients that can prevent their propagation via mating. We have shown that, within one month, weekly in-office application of Tea Tree Oil dramatically decreased the concentration of *demodex* in the patient's eyelid. Eradication of *demodex* has not, to our knowledge, been previously achieved by lid hygiene with ordinary shampoo alone within twelve months.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being placed upon illustrating the principles of the invention.

FIG. 4A through FIG. 4G show migration of *Demodex* resulting from Lid Scrub with TTO.

FIG. 6A shows conjunctiva and FIG. 6B shows lashes before TTO treatment.

FIG. 6C shows conjunctiva and FIG. 6D shows lashes after TTO treatment.

DETAILED DESCRIPTION OF THE INVENTION

Figure 1A:
FIG. 1 represents In Vitro Live and Dead Status of *Demodex*. The same *demodex* was photographed before (FIGS. 1 A, C, and E) and 5 min later (FIGS. 1 B, D, and F).
Figure 1B:
Figure 1C:
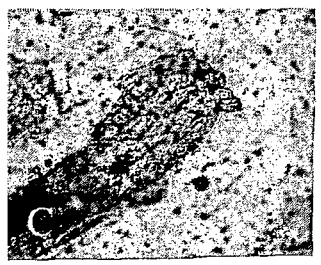
Figure 1D:
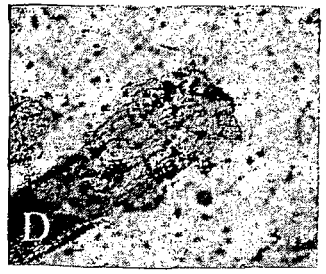
Figure 1E:
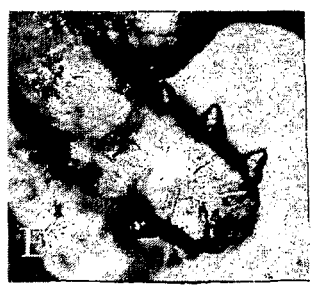
Figure 1F:

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The use of Tea Tree Oil in proximity to the eye appears to be previously unknown. Although warnings that Tea Tree Oil and other isoprenoidal essential oils should be kept away from the eye are found on Material Safety Data Sheets and containers of commercially available samples of these oils, we have now discovered a method of using these compositions to treat ocular *demodex*, blepharitis, and disorders affecting facial skin, even in areas near the eyes.

Disclosed herein is our discovery that, in 7 out of 9 patients in our study, a combination of both weekly in-office eyelid and lashes scrub with fifty percent (50%) Tea Tree Oil and at-home daily lid scrub with Tea Tree Oil shampoo can eradicate ocular *demodex* in one month.

Some results of our in vitro and in vivo testing are first summarized here, with a detailed description of methods and results provided below. The result of one in vitro killing effect test proved that weekly scrub of TTO is capable of killing *demodex* within a few minutes, and its killing effect is concentration-dependent. In order to prove its in vivo killing effect and tolerance, we tested 100% and 50% TTO on patients with ocular *demodex*. We achieved the therapeutic effect defined by bringing the *demodex* counting to zero (0) in five (5) patients in four (4) weeks. The shorter duration of 4 weeks, which is close to one life cycle of *demodex*, further suggests that the killing is strong enough to prevent their propagation via mating. In contrast, the conventional treatment with daily lid scrub using Baby Shampoo could not kill *demodex*.

In an attempt to search for a more effective agent to eradicate ocular *demodex*, a number of known essential oils were tested in vitro. In addition to Tea Tree Oil, we found that Caraway Oil and Dill Weed Oil could each kill *demodex* within 25 minutes.

In addition to testing the effectiveness of isoprenoidal essential oils in killing *demodex*, we isolated and purified many components of these oils and tested the components, as well as other substances, for use in our disclosed method of treatment.

Disclosed herein is our discovery of an effective method for treating ocular *demodex* or *demodex*-induced blepharitis, rosacea, acne, and meibomian gland dysfunction in patients in need of relief, the method comprising: administrating to the patient a composition comprising a therapeutically effective amount of a substance chosen from at least one of: an isoprenoidal essential oil, such as, for example, Tea Tree Oil, Caraway Oil, Dill Weed Oil and Dill Seed Oil; alpha-Terpineol; Cardinene; d-Carvone; l-Carvone; (S)-(+)-Carvone hydrate; gamma-Terpinene; alpha-Terpinene; 1,8-Cineole; 1,4-Cineole; alpha-Terpineol; para-Cymene; alpha-Pinene; Limonene, in particular (R)-(+)-Limonene, Dipentene, (+)-cis-Limonene 1,2-epoxide, and (4R)-Limonene 1,2-epoxide, (±)-Limonene oxide, (R)-(+)-Limonene, (S)-(−)-Limonene, and (+)-trans-Limonene 1,2-epoxide; alpha-Thugene; Eucalyptol; (+)-Ledene; 8-Terpinolene, Acetaldehyde, 3-Isopropoxyphthalide, 3-Propoxyphthalide, Cuminic Aldehyde; and Myrcene, also known as 7-methyl-3-methyleneocta-1,6-diene, furfurol, and combinations thereof, and pharmaceutically acceptable salts thereof. Each of the foregoing disclosed substances that comprise the composition are active ingredients.

As the terms are used herein, "active ingredient," "active agent," and "therapeutically effective substance" have the same meaning and are used interchangeably. Further, the terms "composition of the invention", "formulation of the invention", "disclosed composition", and "disclosed formulation" have the same meaning and are used interchangeably.

The names, structural formulas, molecular formulas, CAS Registry numbers, boiling points and flash points of different compounds of essential oils are provided in Table 1. According to one embodiment of the invention, an active ingredient of the disclosed composition is chosen from at least one of the compounds listed in Table 1, alone or in combination with other compounds from Table 1.

In another embodiment of the invention, an active ingredient of the disclosed composition is chosen from at least one of the compounds listed in Table 1 and at least one essential oil. Any of the various disclosed formulations can be included in a kit for in-office treatment and in a kit for at-home treatment of ocular *demodex*, *demodex*-induced blepharitis, rosacea, acne, and meibomian gland dysfunction. Any of the various disclosed formulations can also be included in a kit for in-office treatment and in a kit for at-home treatment of an infestation chosen from sarcoptic mange, demodectic mange, chorioptic mange, notoedric mange, and cheyletiella mite infestation on a mammalian animal

TABLE 1

| Synonyms: | gamma-Terpinene | α-terpinene | δ-Terpinolene | p-Cymene | |
|---|---|---|---|---|---|
| Structure | | | | | |
| Molecular Formula | $C_{10}H_{16}$ | $C_{10}H_{16}$ | $C_{10}H_{16}$ | $C_{10}H_{14}$ | |
| Formula Weight: | 136.23 | 136.1 | 136.1 | 134.22 | |
| Registry number (RN, CAS): | 99-85-4 | 99-86-5 | 586-62-9 | 99-87-6 | |
| Boiling point | 182° C. | 173-175° C. | 184-185° C. | 176-178° C. | |
| Flash point | 51° C. | Not available | Not available | 47° C. | |
| Synonyms: | (+)-cis-Limonene 1,2-epoxide | (4R)-Limonene 1,2-epoxide | (±)-Limonene oxide, | (R)-(+)-Limonene | (S)-(−)-Limonene |
| Structure | | | | | |
| Molecular Formula | $C_{10}H_{16}O$ | $C_{10}H_{16}O$ | $C_{10}H_{16}O$ | $C_{10}H_{16}$ | $C_{10}H_{16}$ |
| Formula Weight: | 152.23 | 152.23 | 152.23 | 136.23 | 136.23 |
| Registry number (RN, CAS): | 4680-24-4 | 203719-54-4 | 1195-92-2 | 5989-27-5 | 5989-54-8 |
| Boiling point | Not available | Not available | 113-114° C./50 mm Hg | 175.5-176° C. | 175-177° C. |
| Synonyms: | 1-Terpinen-4-ol | 1,8-Cineole | 3-ISOPROPOXY-PHTHALIDE | 3-PROPOXY-PHTHALIDE | |
| Structure | | | | | |
| Molecular Formula | $C_{10}H_{18}O$ | $C_{10}H_{18}O$ | $C_{11}H_{12}O_3$ | $C_{11}H_{12}O_3$ | |
| Formula Weight: | 154.25 | 154.25 | 192.22 | 192.22 | |
| Registry number (RN, CAS): | 562-74-3 | 470-82-6 | 99865-50-6 | 99865-51-7 | |
| Boiling point | 212° C. | 176-177° C. | Not available | Not available | |
| Flash point | 82° C. | Not available | Not available | Not available | |

TABLE 1-continued

| Synonyms: | Dipentene (±)-Limonene | 1,4-Cineole | (R)-(−)-Carvone | (S)-(+)-Carvone | (S)-(+)-Carvone hydrate |
|---|---|---|---|---|---|
| Structure | | | | | |
| Molecular Formula | $C_{10}H_{16}$ | $C_{10}H_{18}O$ | $C_{10}H_{14}O$ | $C_{10}H_{14}O$ | $C_{10}H_{16}O_2$ |
| Formula Weight: | 136.23 | 154.25 | 150.22 | 150.22 | 168.23 |
| Registry number (RN, CAS): | 138-86-3 | 470-67-7 | 6485-40-1 | 2244-16-8 | 60593-11-5 |
| Boiling point | 170-180° C. | Mp: −46° C. | 227-230° C. | 96-98° C./10 mm Hg | 157-158° C./14 mm Hg |

| Synonyms: | (+)-Ledene | Acetaldehyde | Furfurol | Cuminic aldehyde, | (+)-trans-Limonene 1,2-epoxide |
|---|---|---|---|---|---|
| Structure | | | | | |
| Molecular Formula | $C_{15}H_{24}$ | $C_2H_4O$ | $C_5H_4O_2$ | $C_{10}H_{12}O$ | $C_{10}H_{16}O$ |
| Formula Weight: | 204.35 | 44.03 | 98.10 | 148.20 | 152.23 |
| Registry number (RN, CAS): | 21747-46-6 | 75-07-0 | 98-01-1 | 122-03-2 | 6909-30-4 |
| Boiling point | 268-270° C. | 22-24° C. | 162° C. | 235.5° C. | Not available |

Components of Caraway Oil: Acetaldehyde, Cuminic aldehyde, Furfurol, Carvone, Limone In addition to Tea Tree Oil, other essential oils and compounds listed in Table 1, either alone or in combination, can be added to a shampoo and included in a kit for in-office or for at-home treatment of ocular *demodex*, blepharitis, rosacea, acne, and meibomian gland dysfunction. Alternatively, essential oils and compounds listed in Table 1 can be included in the kit along with directions for adding an effective quantity of the essential oil or compound to a shampoo, water, suspension, gel or powder to produce a formulation for treatment of a human or animal. Preferred ingredients are those with higher boiling points, because they are less toxic and more effective in killing.

In addition, we have carried out further experiments to show that Terpinen-4-ol is indeed an active ingredient. (See Table 2 below, Survival Time of *Demodex* in Different Solutions, which illustrates the dose-dependent relationship of TTO.) Furthermore, we have determined that (R)-(+)-Limonene (from Sigma) and Eucalyptol (from Fluka/Sigma) are not as effective as TTO (See Table 3). However, (+) Carvone is as effective as TTO (See Table 3).

TABLE 3

Table Killing effect of different agents on Demodex (Time in minutes)

| (+)-Carvone | | | (+)-Limonene | | CWO | Pilocarpine | | TTO | | |
|---|---|---|---|---|---|---|---|---|---|---|
| 100% | 50% | 25% | 97% | Eucalyptol | 10% | 2% | 4% | (100%) | (50%) | (25%) |
| 5 | 8 | 25 | 52 | 30 | 5 | 150 | 150 | 3 | 34 | 30 |
| 4 | 10 | 20 | 67 | 35 | 13 | 150 | 150 | 5 | 30 | 27 |
| 3 | 11 | 23 | 50 | 40 | 14 | 150 | 150 | 3 | 25 | |

TABLE 3-continued

Table Killing effect of different agents on Demodex (Time in minutes)

| (+)-Carvone | | | (+)-Limonene | | CWO | Pilocarpine | | TTO | | |
|---|---|---|---|---|---|---|---|---|---|---|
| 100% | 50% | 25% | 97% | Eucalyptol | 10% | 2% | 4% | (100%) | (50%) | (25%) |
| 5 | 16 | | 110 | 42 | 16 | 150 | | | | |
| 4 | 13 | | 55 | | 12 | | | | | |
| | | | | | 13 | | | | | |
| Average: | | | | | | | | | | |
| 4.2 | 11.6 | 22.7 | 66.8 | 36.8 | 12.2 | 150 | 150 | 3.7 | 29.7 | 28.5 |

As described above, the compositions and methods according to embodiments of the invention can be used on any vertebrate with skin. Examples of such vertebrates include mammals, for example, human, bovine, porcine, canine, feline, and avian.

Methods of Administration

To achieve the improvements described herein, the present invention provides for a method of topically administering a disclosed composition to an affected area of the skin, to the eyelid margin, or to the eyelashes. An affected area of the skin is one which shows symptoms of the patient's disorder, symptoms such as, e.g., inflammation, itching, pain, tingling, burning, discoloration, surface irregularities, and/or an erratic accumulation of fibrous tissue. Symptoms may arise from any of the afore-mentioned disorders, or from a number of types of skin traumas, e.g., laceration, burn, surgery, infection, acne, and chemical facial peel. Disclosed compositions of the invention can be administered in a variety of ways.

In a one embodiment, the compositions of the present invention are administered by scrubbing an eyelid margin and lashes of the patient, or an affected area of the skin, with the composition. A protocol for this form of administration is described in detail below. A scrub of the eyelid and lashes or the affected area of the skin with a disclosed composition can be accomplished by using a cloth, a sponge, cotton swabs, other applicators, or the fingers. A disclosed composition can also be administered along with shampoo, in particular, a shampoo comprising at least one active ingredient, such as Tea Tree Oil, another essential oil, and a compound listed in Table 1, either alone or in combination with other active ingredients.

In another embodiment, the compositions of the invention are administered by contacting an eyelid margin and lashes of the patient or an affected area of the skin with the composition, allowing the composition to adhere to the eyelid margin and lashes or to the skin, and leaving the composition adhering to the eyelid margin and lashes or to the skin without washing for a period of time sufficient to show an improvement in the condition.

Disclosed variations of the method of contacting the eyelid margin and lashes or the affected area of the skin include smearing or coating the composition onto the skin, in the same manner in which one might apply eye liner makeup to the lid margin. We have tested this mode in addition to other modes, and found these methods to be very effective. Other variations of the disclosed method of application include the use of an applicator or a squeezable tube filled with the composition. The eyelid, eye lashes, and any affected area of skin on a human or other mammal can also be scrubbed with an effective amount of one or more of the disclosed active ingredients.

The administration according to another embodiment is an administration that is a combination of two or more routes of administration.

In administering a disclosed composition to an animal other than human, it may be necessary to anesthetize or tranquilize the animal prior to applying the composition to the face. If anesthesia is necessary, the treatment can be done in the veterinarian's office.

The in-office treatment of the animal can be followed up with an at-home treatment of the affected animal by using a disclosed kit comprising at least one of a shampoo, gel, solution, suspension, or other disclosed formulation according to the instructions included in the kit. Alternatively, the instructions in the kit may include directions for preparing a formulation such as a shampoo, lotion, or gel for treating the animal, the formulation to be prepared from a disclosed active ingredient and water or a commercially available shampoo, lotion or salve.

While the disclosed methods of treating ocular *Demodex* or *Demodex*-induced blepharitis, rosacea, acne, and meibomian gland dysfunction may include administration of one or more of the disclosed substances, the substance or combination of substances may also include a physiologically acceptable salt of one or more of the substances. In one embodiment the substance or combination of substances is administered in a pharmaceutical composition together with one or more adjuvants, excipients, carriers and/or diluents.

Therefore, in another embodiment, the present invention also relates to pharmaceutical compositions which include a suitable pharmaceutical carrier. Any of the disclosed compositions may be administered with a suitable pharmaceutical carrier, the choice of which depends on the route of administration and the condition of the patient.

The terms "suitable pharmaceutical carrier," "pharmaceutically acceptable carrier," and grammatical variations thereof, as they refer to compositions, carriers, diluents and reagents, are used herein interchangeably. As the terms are used herein, "suitable pharmaceutical carrier" and "pharmaceutically acceptable carrier" refer to non-toxic materials that do not interfere with the effectiveness of the biological activity of active ingredients, and represent that the materials are capable of administration to or upon a vertebrate with a minimum of undesirable physiological effects such as nausea, dizziness, gastric upset and the like.

The preparation of a pharmacological composition that contains active ingredients dissolved or dispersed therein is well understood in the art and need not be limited based on formulation. Liquid preparations include solutions, suspensions, gels, colloids, hydrogels, and emulsions, for example, water or water-propylene glycol mixtures. Solid forms such as powders suitable for suspending in liquid or gels prior to use can also be prepared. The preparation can also be emulsified.

A disclosed composition can be mixed with excipients that are pharmaceutically acceptable and compatible with the composition, and in amounts suitable for use in the therapeutic methods described herein. Suitable excipients include, for example, water; saline; lubricants such as corn oil, olive oil, glycerol, petroleum jelly; dextrose; ethanol, or the like, and combinations thereof.

In one embodiment a disclosed composition for topical administration to the skin contains a binder such as gum tragacanth, acacia, corn starch or gelatin. Various other materials may be present as coating or to modify the physical form of the dosage unit.

In addition, if desired, the composition can contain minor amounts of auxiliary substances such as pH buffering agents and the like which enhance the effectiveness of the active ingredient or the safety of the administrative route. Details on techniques for formulation and administration may be found in the latest edition of *Remington's Pharmaceutical Sciences* (Maack Publishing Co., Easton, Pa.).

Any of the above formulations and shampoos may be included in a kit for in-office treatment or in a kit for at-home treatment of the patient. Such a kit may also include an applicator for a disclosed formulation.

Therapeutically Effective Amount and Dosage

A disclosed composition is administered to a patient in a therapeutically effective amount. As used herein, the terms "therapeutically effective amount" and "therapeutically effective dose" have the same meaning and refer to the amount of an active agent, for example, terpinene-4-ol, a therapeutically effective substance, required to be administered in order to induce a desired result in the patient. That result may be alleviation or amelioration (complete or partial) of the symptoms of the condition of the patient in need of treatment, any other desired improvement in the patient's symptoms, disease or condition, or prophylaxis or delay in the onset of symptoms of ocular *Demodex* or *Demodex*-induced blepharitis, rosacea, acne, and meibomian gland dysfunction.

The terms "method of treating" or "method for treating" when used in relation to the present invention means amelioration, prevention or relief from the symptoms and/or effects associated with a condition in an individual. The person of ordinary skill in the medical art recognizes that "prevention" of the symptoms and/or effects associated with a disease or condition is not an absolute term. In the medical art it is understood to refer to the prophylactic administration of a drug to substantially diminish the likelihood or seriousness of the condition.

As used herein, the term "therapeutically effective amount" may also refer to the quantity of active agent or therapeutically effective substance, such as Terpinen-4-ol, or (+)-Carvone, the administration of which results in improvement in the patient's symptoms, disease, or condition, where little or no improvement would occur in the absence of the active agent. Typically, the therapeutically effective substance is administered for a sufficient period of time to achieve the desired therapeutic effect.

Therapeutic efficacy and the therapeutically effective dose of a particular substance may be determined by using standard pharmacological procedures in experimental animals and with no more than routine trials or routine experimentation.

For example, the term "therapeutically effective amount" is intended to mean an amount of a disclosed composition that will alleviate the symptoms or eradicate *Demodex* or decrease *Demodex* in comparison to the level prior to administration of the composition. Evaluation of symptoms can be performed using any medically acceptable procedures known to those of skill in the medical arts.

According to the method of the invention, a disclosed compound can also be administered for treating the symptoms of the pathologies associated with ocular *Demodex* or *Demodex*-induced blepharitis, rosacea, acne, and meibomian gland dysfunction, or for inhibiting the onset of such symptoms.

The dosage regimen of the disclosed compositions is selected in accordance with a variety of factors including type, species, age weight, sex and medical condition of the patient; the severity of the condition to be treated; the route of administration; and the particular composition employed. Consideration of these and other relevant factors are well within the purview of the ordinarily skilled clinician for determination of an appropriate therapeutic regimen according to an embodiment of the invention, to attenuate or arrest the progress of the condition.

Generally, a therapeutic amount of a disclosed compound for use on a human or animal is in the range of from about 1 microgram/day to about 1 gram/day. This dosage regimen may be adjusted to provide the optimal therapeutic response.

In embodiments of the above-described methods, the disclosed compositions may be administered either alone or in combination with one or more additional bioactive agents, or other therapeutically effective substances. As used herein, the terms "therapeutically effective substance" or "therapeutic substance" include:

(i) Compounds and compositions recognized in the official United States Pharmacopoeia, the official Homeopathic Pharmacopoeia of the United States, or the official National Formulary, or any supplement of any of them;

(ii) Compounds and compositions intended for use in the diagnosis, cure, mitigation, treatment, or prevention of disease in man or other animals; and (iii) Compounds and compositions (other than food) intended to affect the structure or any function of the body of man or other animals.

A composition disclosed for use in a method according to an embodiment of the invention is intended to include all pharmaceutically acceptable salt, ester, free acid and lactone forms of the compounds therein which have therapeutic activity. Therefore, the use of such salts, esters, free acids and lactone forms are included within the scope of this invention.

The invention is described in more detail in the following examples. These examples are provided by way of illustration and are not intended to limit the invention in any way.

In a preferred embodiment of the invention, in order to eradicate *demodex*, the eyelids and lashes of the patient in need of treatment should be scrubbed weekly with a composition comprising an isoprenoidal essential oil such as Tea Tree Oil. This in-office treatment should be followed by twice daily, and then daily at-home eyelid and lashes scrubs with a shampoo containing an isoprenoidal essential oil such as Tea Tree Oil. The regimen should continue for a period of time sufficient to eradicate the *Demodex* infestation. According to one embodiment, disclosed protocols for lid scrubs are as follows.

Weekly In-Office EyeLid and Lashes Scrub:

1. Put about one drop of 0.5% proparacaine into each eye.

2. Dip about 80% of the swab tip (for example, a cotton tipped swab) into the Tea Tree Oil (TTO) so that the swab will not absorb too much liquid.

3. Make about 6 strokes at the root of the lashes from one end of the lid to the other with a medium (not too hard but not too light) pressure.

4. Use a dry swab to clean the lid margin for one stroke to make sure the excessive solution, if any, will not get into the eye.

5. About five minutes later, clean the dandruffs in the lash root with a dry swab with about 5 strokes with a medium pressure. This will remove dandruffs which are already loose but still adherent on the lashes as a result of the first TTO treatment.

6. Wait for approximately another 5 minutes; apply the second TTO treatment in exactly the same way as Step #2 to #4. Because mites tend to move slowly out under the stimulation of TTO, the subsequent TTO treatments can cause increased therapeutic effects.

7. After about another 10 minutes, apply the third TTO treatment as Step #2 to #4.

8. The patient should be observed in the office for approximately another 15 minutes to see if there is any irritation. If so, rinse the eye with a non-preserved saline solution, for example, UNISOL® immediately.

9. Repeat the same procedure once every week for 4 weeks, or until the desired level of improvement or eradication of *demodex* is achieved.

Domestic (Home) EyeLid and Lashes Scrub:

1. Squeeze 0.5 ml of Tea Tree Shampoo at both middle fingers, mix with water to generate the shampoo foaming.

2. Close the eyes and massage the Tea Tree shampoo on both eyelids and lashes with a medium pressure for about 3 to about 5 minutes.

3. Rinse the lids and lashes with a lot of clean water.

4. Dry the lids and eyes with clean towel.

5. Apply the procedure twice daily within one month; then apply the procedure daily.

Other Instructions:

1. Abandon long-used make ups. Wash the hair, the face, nostrils, the external ear and neck with Tea Tree shampoo the way you wash the face daily. Facial cream can be use in a normal fashion, however, take care to not contaminate the face cream. Contamination could occur by, for example, dipping your fingers into the jar of cream, applying the cream to your face and then dipping the same fingers into the jar again. In order to avoid contaminating the cream it is best to put the cream into an applicator or squeezable container with an opening to dispense the cream, and then squeeze a quantity of the face cream onto your hand.

2. Wash the entire bedding and pillows with hot water or warm dryer immediately after the first in-office treatment, and then wash them regularly no less than once every week.

3. If your spouse or another family member also notes similar eye irritation with dandruffs in the lashes, involve him or her in the hygiene described above.

Experimental Study: In Vitro and In Vivo Killing of Ocular *Demodex* by Tea Tree Oil Abstract of this Study:

Judging the cessation of body and leg movements, we measured the time needed for several agents to kill live adult *demodex* retrieved from epilated lashes with cylindrical dandruff. Our result showed that *Demodex* folliculorum survived for more than 150 min (no effect) in 10% povidone iodine, 75% alcohol, 50% baby shampoo, 4% pilocarpine, pre-treatment with 50% baby shampoo or 10% SDS followed by 10% povidone iodine, or pre-treatment with 10% povidone iodine followed by 75% alcohol. However, the survival time was significantly shortened to within 15 min for 100% alcohol, 100% tea tree oil (TTO), 100% caraway oil, and 100% dill weed oil. TTO's in vitro killing effect was dose-dependant. A similar result was obtained for *Demodex brevis*. Lid scrub with 50% TTO, but not with 50% baby shampoo, can stimulate *demodex* to move out to the skin. The *demodex* count per 8 lashes did not reach zero in any of the 7 patients receiving daily lid scrub with diluted baby shampoo for 40 to 350 days. In contrast, the *demodex* count dropped to zero in 4 weeks in 7 of 9 patients receiving office lid scrub with 50% TTO and home lid scrub with TTO shampoo without recurrence. We thus conclude that *demodex* is resistant to a wide range of solutions thought to be antiseptic. Weekly lid scrub with 50% TTO and daily lid scrub with TTO shampoo is effective in eradicating ocular *demodex*.

Materials and Methods

Materials

10% povidone iodine, 75% and 100% alcohol, mineral oil, 10% SDS, and TTO were from Sigma (Milwaukee, Wis., USA), 4% Pilocarpine solution was from Bausch & Lomb (Tampa, Fla., USA), caraway oil and dill weed oil were from Essential Oil Company (Portland, Oreg., USA). TT shampoo was from Kato Sales, Inc. (Altamonte Springs, Fla., USA). TTO was diluted with mineral oil into different concentrations.

Statistical Analysis

The data were reported as means±S.D. and analyzed by Microsoft EXCEL® (Microsoft, Redmont Wash.). The data between groups were evaluated by two-tailed t test where $p<0.05$ was considered statistically significant.

In Vitro Killing

Under the microscope, if the epilated lash contained live *demodex*, different solutions were added to the coverslip edge. The movement of *demodex* body and legs was continuously observed for 150 minutes. The survival time (ST) (Table 2 below) was counted from the time when the solution was added to the time when the movement ceased (See FIG. 1) The average ST tested for a given solution in a number of mites was used to compare the in vitro killing effect. If *demodex* remained alive at the end of 150 minutes, this value was denoted as no effect. Because *demodex* in an earlier life stage was more vulnerable, we only tested adult *demodex* that had 4 pairs of well developed legs and stumpy body. Because *demodex* buried in cylindrical dandruff (CD) might preclude the killing effect, we only tested *demodex* of which the whole body was fully exposed to the test solution.

FIG. 1 is a microphotograph showing in vitro Live and Dead Status of *Demodex*. The same *demodex* was photographed before (A, C, and E) and 5 min later (B, D, and F). The *demodex* was judged to be "live" by vivid movement of the body (A, B) or legs (C, D). In contrast, the *demodex* was judged to be "dead" by the lack of movement (E, F). Furthermore, all 8 legs of the dead mite were stretched apart (E, F) distinctively different from the live one (C, D).

TABLE 2

Survival Time of Demodex in Different Solutions

| | Solution | | | | | | | |
|---|---|---|---|---|---|---|---|---|
| | 50% BS | 10% PI | 75% Alc | MO | 4% Pilo | Mix 1 | Mix 2 | Mix 3 |
| ST (min) | 150 | 150 | 150 | 150 | 150 | 150 | 150 | 150 |
| DN | 9 | 4 | 8 | 5 | 3 | 6 | 5 | 6 |

TABLE 2-continued

Survival Time of Demodex in Different Solutions

| | Solution | | | | | |
|---|---|---|---|---|---|---|
| | 100% Alc | 10% TTO | 25% TTO | 50% TTO | 100% TTO | 100% CWO | 100% DWO |
| ST (min) | 3.9 ± 1.2 | 150 | 34.7 ± 4.3 | 14.8 ± 9.5 | 3.7 ± 0.8 | 4.4 ± 2.3 | 14.0 ± 8.3 |
| DN | 7 | 5 | 5 | 11 | 21 | 16 | 5 |

[Note]:
ST: survival time recorded in minute,
DN: number of demodex tested,
BS: baby shampoo,
MO: mineral oil,
PI: povidone iodine,
Alc: alcohol,
Mix 1: 50% BS in water for 30 min followed by 10% PI,
Mix 2: 10% SDS in water for 30 min followed by 10% PI, and
Mix 3: 10% PI for 30 min followed by 75% Alc,
TTO: tea tree oil.
CWO: caraway oil,
DWO: dill weed oil and
Pilo: pilocarpine.

Results: In Vitro Killing Effect

We first surveyed a number of agents listed in Table 2 (above), and noted that 50% baby shampoo, 100% mineral oil, 75% alcohol, 10% povidone iodine, or 4% Pilocarpine could not kill *demodex* in 150 minutes. In contrast, 100% alcohol killed it in 3.9±1.2 minutes. Because *demodex* is frequently trapped in the CD, which consists of cellular debris made of lipids and keratins (English F P, Nutting W B. Demodicosis of ophthalmic concern. *Am. J. Ophthalmol.* 1981; 91:362-72.), we also examined whether a pretreatment with such a detergent as 10% SDS or 50% baby shampoo might promote the killing effect of other agents. The results showed that none of such pre-treatments for 30 minutes could facilitate the killing by subsequent application of either 10% povidone iodine or 75% alcohol. In contrast, 100% of TTO, caraway oil or dill weed oil killed mites in 3.7±0.8, 4.4±2.3, and 14.0±8.3 minutes, respectively. Furthermore, the killing effect of TTO was dose-dependent, i.e., being 14.8±9.5, 34.7±4.3, and 150 minutes for 50%, 25% and 10% of TTO, respectively ($p<0.01$). These results indicated that 100% TTO, 50% TTO, 100% caraway oil and 100% dill weed oil exerted effective in vitro killing within 15 minutes. 50% TTO and 10% TTO also exerted a similar killing of *D. brevis* (not shown).

In Vivo Studies—Patients

This study followed the Tenets of Helsinki Declaration of Human. All patients had received routine complete eye examination and external photography, and found to have ocular *demodex* (see below). They were not using topical or systemic anti-inflammatory and anti-bacterial medications. Seven patients had practiced eyelid scrub with diluted baby shampoo at least once daily. Nine patients received lid scrub with TTO in the office and daily eyelid and lashes scrub with Tea Tree Oil shampoo (TT shampoo) at home. As the term is used herein, "lid scrub" refers to scrubbing of both eyelid and eyelashes.

Lash Sampling and *Demodex* Counting

For each patient, we epilated a total of 8 lashes with CD, two from each eyelid, and covered them with a coverslip on a slide. Under the microscope, if the lash did not retain CD, BSS was added; if it contained CD, 100% alcohol was added to the edge of the coverslip to dissolve CD. The total number of *demodex* counted from these 8 lashes was used for comparison.

Lid Scrub with TTO

In the office, after a drop of 0.5% proparacaine was instilled to each eye, a cotton tip dipped in 50% TTO was used to scrub the lash roots from one end to the other of an eyelid with a medium pressure, counted as one stroke. A total of 6 strokes were applied to each lid. A dry cotton tip was then used to remove excess TTO from the lid margin. Because TTO scrub not only loosened CD but also stimulated *demodex* to move out to the skin (see Results), a dry cotton tip was used to remove CD 5 minutes later. After another 5 minutes, the second lid scrub with TTO was applied in the same manner. After 10 minutes of rest, the third TTO lid scrub was applied. If there was any irritation, the eye was rinsed with non-preserved saline.

Home Lid Scrub and Other Instructions

At home, the patient was asked to mix 0.5 ml of TT shampoo with tap water in both middle fingers. With eyes closed, the eyelids and lashes were massaged with a medium pressure for 3 to 5 minutes. The skin was then rinsed with clean water and dried with a towel. Such at home lid scrub was practiced twice daily for one month and then once daily thereafter. In addition, the patient was also instructed to discard used facial make-ups, and wash the hair, the face, nostrils, the external ear and the neck with TT shampoo daily. The bedding and pillow cases were washed with hot water and dried in a heated dryer immediately after the first office scrub, and once a week thereafter. If the spouse also complained of similar eye irritation, the same at home lid scrub was also practiced.

In Vivo Killing by Lid Scrub with Diluted Baby Shampoo

Figure 2:
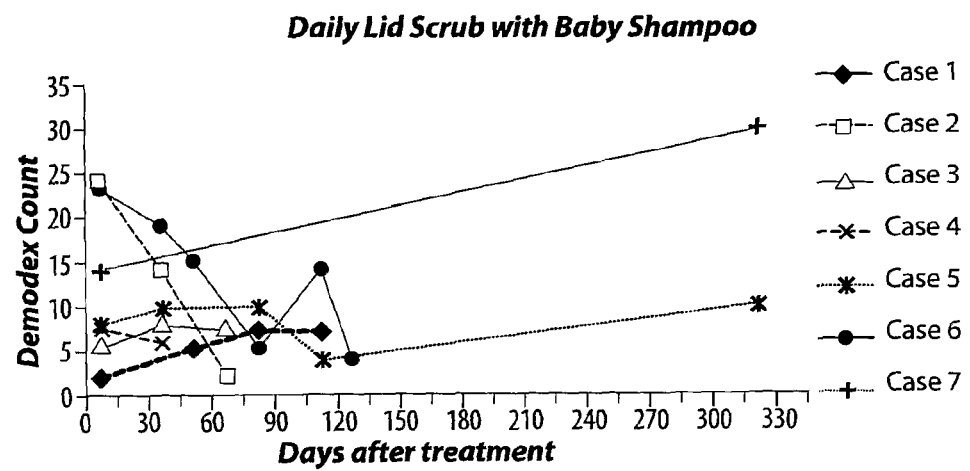
FIG. 2 depicts *Demodex* Counts in Patients Receiving Lid Scrub with Diluted Baby Shampoo.

FIG. 2 depicts *Demodex* Counts in Patients Receiving Lid Scrub by Diluted Baby Shampoo. In these 7 patients, their serial *demodex* counts did not drop to zero despite daily lid scrub with diluted baby shampoo when practiced for more than one month.

Cases #3, #4, and #5 maintained a constant number of *demodex* after 40 to 350 days of lid hygiene. Case #1 and #7 actually showed an increase of *demodex* after 110 to 350 days. Only Case #2 and #6 showed a decrease of *demodex* after 64 and 125 days of lid hygiene, respectively, but never reached zero.

In Vivo Killing by Lid Scrub with TTO

We recently confirmed that lashes with cylindrical dandruff (CD) is pathognomonic for ocular *demodex*. It is thus important to get rid of CD, which harbors *demodex*. Studies show that lid hygiene with shampoo reduces *demodex* counts but does not eradicate *demodex* Lid hygiene with shampoo cleans only CD extending outside the skin, but does not eradicate *demodex* buried deep under the skin. See Y. Y. Gao et al., *Invest Ophthalmol Vis Sci.* 2005 September; 46 (9): 3089-94, the teachings of which are incorporated herein by reference in its entirety. Applicants have developed a more effective therapy, not by solely cleansing but rather by killing *demodex* buried deep in the follicle.

Figure 3A:
FIG. 3A through FIG. 3 D depict different results of Lid Scrub with TTO and with Baby Shampoo in a patient presenting with symmetrical signs of CD in both eyelids.
Figure 3B:
Figure 3C:
Figure 3D:

In a patient presenting with symmetrical signs of CD in both eyelids, lid scrub with 50% TTO in the right eye and with 50% baby shampoo in the left eye for 5 min equally cleaned off CD (FIGS. 3A and 3B). However, *demodex* was found on the skin surface adjacent to the lashes (FIG. 3C, arrows), and *demodex* tail was seen protruding from the lash root (FIG. 3C, arrowheads) in the TTO treated eye, but not in the baby shampoo treated eye (FIG. 3D). Furthermore, the skin in the eye receiving TTO was redder than that receiving baby shampoo. These findings suggested that lid scrub with TTO did not merely mechanically remove CD from the lash root, but might attract mites to move out to the skin.

To examine this possibility, we epilated lashes with diffuse CD (FIG. 4A) and found that *D. folliculorum* clustered around the lash follicle (FIG. 4D). After office lid scrub with 50% TTO, the lashes were free of CD (FIG. 4B). Interestingly, tails were protruding from the lash root (FIG. 4B, arrow). When these lashes were epilated, *D. folliculorum* was found on the lash trunk close to the skin surface, i.e., away from the lash follicle (FIG. 4E). When such lash was rotated by a forceps before epilation, we noted several mites migrating along the lash trunk (FIGS. 4F and 4G). If no home lid scrub was subsequently practiced, CD returned in one week (FIG. 4C). If the lashes were scrubbed with baby shampoo, simple mechanical rotation did not stimulate *demodex* to move out (not shown). These results indicated that lid scrub with 50% TTO, but not baby shampoo, indeed stimulated *demodex* to migrate from CD embedded inside the skin.

Figure 5:
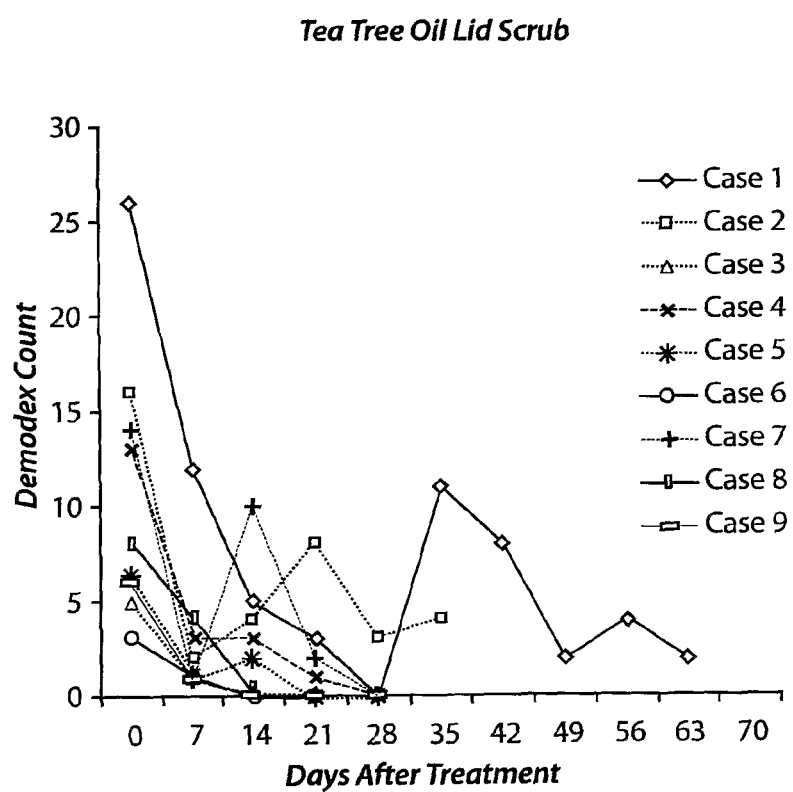
FIG. 5 is a graphical representation of *Demodex* counts in patients receiving Lid Scrub with TTO.

Because lid scrub with 50% TTO did not kill mites buried deep in the skin, and because if no lid scrub was carried out at home, CD quickly returned in one week, we advocated that weekly office lid scrub with 50% TTO be followed by daily home eyelid and lash scrub with TT shampoo in 9 patients (FIG. 5). The results showed that the *demodex* count dropped to zero in 3 weeks in 5 patients and in 4 weeks in another 2 patients without any recurrence one month later. These 7 patients were younger (59.86±8.7 year-old), and had a mean count of 7.9±4.1 before treatment. In the remaining 2 patients, Case No. 1 and Case No. 2, the count didn't reach zero, and showed a rebound 35 days and 14 days after treatment, respectively. They were a 68 year old patient and an 81 year-old patient, and had a higher count of 26 and 16, respectively, before treatment. The rebound count was less than the previous one, and the interval between rebounds was 2 to 3 weeks.

Discussion

In this report, we were surprised to note that the *demodex* count of all 7 patients receiving daily lid hygiene with baby shampoo never reached zero in a period between 40 and 350 days, i.e., beyond one life cycle (FIG. 2). This result together with those published earlier (Junk A K, et. al. "Topical administration of metronidazole gel as an effective therapy alternative in chronic *Demodex blepharitis*—a case report," *Klin. Monatsbl. Augenheilkd.* 213:48-50; (1998); Fulk G W, et. al., "Pilocarpine gel for the treatment of demodicosis—a case series," *Optom. Vis. Sci.* 73:742-5 (1996)) strongly imply that this conventional treatment cannot eradicate *demodex*, a notion also confirmed by the finding that 50% baby shampoo did not kill *demodex* in vitro (Table 2). We were also surprised to note that 75% alcohol and 10% povidone iodine, agents known to kill most microbes, could not kill *demodex* in vitro (Table 2). Because prior incubation with 50% baby shampoo or 10% SDS, detergents dissolving oil, before 10% povidone iodine still could not kill *demodex* (Table 2), we believe that the body surface of *demodex* is resistant to povidone iodine.

Although 4% Pilocarpine gel was used to treat *demodex*, it did not kill *demodex* in 150 min (Table 2). In 1970, Norn (Norn M S., *Demodex folliculorum*. Incidence and possible pathogenic role in the human eyelid, *Acta Ophthalmol Suppl* 1970; 108:7-85.) tested 45 different agents and found only few could kill *demodex* within several minutes. They are absolute alcohol, ether, xylol, benzene, Danish (sulfur-containing) ointment, organophosphate-cholinesterase inhibitors, dill weed oil, and caraway oil. Consistent with his finding, we noted that 100% alcohol did kill *demodex* within 3.9±1.2 minutes. Furthermore, 100% of dill weed oil and caraway oil, both being nature essential oils, also killed *demodex* in 14±8.3 and 4.4±2.3 min, respectively (Table 2). Unfortunately, these agents are not amenable for clinical uses because their intrinsic toxicity and irritation to the eye.

We were encouraged by TTO's killing effect, which resembled that of caraway oil and exhibited a clear dose-dependent relationship (Table 2). Although the killing effect of TTO on lice is thought to be mediated by anti-cholinesterase activity (Mills C, et al. Inhibition of acetylcholinesterase by Tea Tree oil, *J Pharm. Pharmacol,* 2004; 56:375-9), it cannot explain its killing effect on nits or *demodex*. Although TTO might cause contact dermatitis and allergy (Simpson E L, et. al., Prevalence of botanical extract allergy in patients with contact dermatitis, *Dermatitis* 2004; 15:67-72.), TTO shampoo is commercially available for treating head lice without an adverse effect. The dermal LD50 in rabbits exceeds 5 g/kg, and undiluted TTO does not produce phototoxic effects on the skin of hairless mice (Ford R A, et. al., Monographs on fragrance raw materials, *Food Chem. Toxico,* 1988; 26:273-415.). TTO patch test does not cause adverse reactions (Brenan J A, et al., Evaluation of patch testing in patients with chronic vulvar symptoms, *Australas. J. Dermatol.,* 1996; 37:40-3.).

It is taught that Tea Tree Oil should be kept away from the eyes. Because of the historic warnings to keep Tea Tree Oil away from the eye, there was no obvious way to use Tea Tree Oil to treat ocular *demodex*, However, even though we had no reasonable expectation of success, we decided to try to develop a method of using TTO to treat ocular *demodex*.

Although both effectively cleaned CD from the lashes, TTO, but not baby shampoo, stimulated *demodex* to migrate from the CD buried inside of the skin (FIG. 3 and FIG. 4). However, if daily lid scrub were not followed, CD returned in one week (FIG. 4).

FIG. 3 shows different results of Lid Scrub by TTO and Baby Shampoo. In a patient presenting with symmetrical signs of CD in both eyelids, lid scrub was performed in the office by 50% TTO in the right eye (A) and by 50% baby shampoo in the left eye (B). In either eye, CD was clean after scrub (C, D), however, *demodex* could be found on the lid margin adjacent to the lashes (C, arrows), and *demodex* tail could be visualized protruding from the lash root (C, arrowheads) after TTO scrub. These findings were not detected in the eye after baby shampoo scrub although the skin surface was less red (D).

FIG. 4 shows migration of *Demodex* by Lid Scrub with TTO. In this eye with diffuse CD found in the lashes before treatment (A), epilation of the lash (marked by arrow) showed a fragment of CD attached to the lash and abundant *demodex* embedded close to the lash follicle (D). After office eyelid and lashes scrub with 50% TTO, the lashes became clean, and totally free of CD, but tails of *demodex* were protruding from the lash roots (B, arrow). Three minutes after eyelid and lashes scrub, free *demodex* was found on the trunk close to the skin surface, i.e., away from the lash follicle in the epilated lash (E). Rotating these lashes (shown in B) before epilation allowed us to detect a group of *demodex* migrating along the lash trunk (F and G). If no eyelid and lashes scrub was carried out at home for one week, CD returned to the lashes one week later (C).

Because mechanical agitation to the lash following TTO scrub was sufficient to stimulate *demodex* to migrate out to the skin, we advocate daily eyelid and lashes scrub with TT shampoo following each office lid scrub with TTO. Because neither 50% baby shampoo nor TT shampoo, of which the concentration of TTO is less than 10%, could kill *demodex* in vitro (Table 2), we believe that home eyelid and lashes scrub acts by arousing *demodex* to move out and eliminating them before *demodex* mating occurs. Although *D. brevis* is also found in lash samples (Ford R A, et. al., Monographs on fragrance raw materials, *Food Chem. Toxicol*, 1988; 26:273-415), it is not mentioned in *demodex* related blepharitis (English F P, et. al., Demodicosis of ophthalmic concern, *Am. J. Ophthalmol.*, 1981; 91:362-72.).

Herein, *D. brevis* was found in patients with blepharitis and exhibited similar susceptibility to TTO killing in vitro.

Using the proposed scrub regimen with TTO and TT shampoo, the *demodex* count was dramatically reduced in one week and reached zero in one month without recurrence in 7 of 9 patients (FIG. 5). The two patients that failed to be eradicated were older, started with a higher *demodex* count, and rebound in an interval of 2 to 3 weeks. Norn (Supra) and our recent studies (manuscript submitted) have noted that patients with a higher *demodex* count tend to be older, suggesting that *demodex* infestation, if untreated, tends to be worsened with age due to continuous propagation by mating. We thus speculate that higher *demodex* infestation produces more CD inside and outside the lash follicle, and more resistant to TTO. If this interpretation were correct, we predict that it is easier to treat *demodex* at an early stage. Alternatively, the failure might be caused by re-infestation by mites migrating from other places of the body or from the spouse. Because the rebound count was less than the previous one, we speculate that continuing the eyelid and lashes scrub regimen might eventually eradicate *demodex*.

Now that ocular *demodex* can be eradicated by eyelid and lashes scrub with TTO, we can begin to investigate its pathogenic role in generating symptoms of irritation, signs of inflammation, and disturbance of the lipid tear film in the future.

"Clinical treatment of ocular *demodex* results in the eradication of *demodex*", Y. Y. Gao, et al., *Br J Ophthalmol.*, 2005 November; 89(11):1468-73, is incorporated herein by reference in its entirety. The clinical study analyzed the outcome of treating ocular demodecosis by lid scrub with Tea Tree Oil. The study included 11 patients with ocular *demodex* who received weekly eyelid and lashes scrub with 50% TTO combined with daily lid hygiene (lid and lashes scrub) with tea tree shampoo. After TTO lid and lashes scrub, the *demodex* count dropped to zero in less than 4 weeks in 8 of 11 patients. Ten of the 11 patients showed different degrees of relief of symptoms and notable reduction of inflammatory signs. Vision improved in 6 of 22 eyes and the lipid spread time was significantly shortened without a change in the lipid film thickness. *Demodex* potentially causes ocular surface inflammation, meibomian gland dysfunction and lash abnormalities. Eyelid and lashes scrub with TTO can effectively eradicate ocular *demodex* and result in subjective and objective improvements. Nine patients (Cases No. 1 to No. 9) underwent the kinetic analysis of tear interference images before and after TTO eyelid and lashes scrub.

After TTO lid scrub, all patients were free of CD. In these 11 patients who received weekly TTO lid scrub plus daily lid scrub with tea tree shampoo, the *demodex* counts dropped sharply in the first week after TTO treatment for all patients. The *demodex* counts dropped to zero in 3 weeks for 6 patients, and in 4 weeks in another 2 patients, and didn't drop to zero in 5 to 9 weeks in 3 patients (Table 4). After weekly office lid scrub with 50% TTO and daily home lid scrub with TTO shampoo, 9 of 11 patients experienced 50% to 100% improvement in symptoms.

TABLE 4

| Case | Age | Sex | Diagnosis | Allergy history | Complaints Before | Complaints After | Uncorrected Vision Before | Uncorrected Vision After | Conjunctival inflammation Before | Conjunctival inflammation After |
|---|---|---|---|---|---|---|---|---|---|---|
| 1 | 68 | F | Recurrent pterygium, lash loss | No | Redness, FBS, itching for 2 years | 80%, redness 100%. FBS, itching, more opening | 20/200 20/200 | Same | +++ | + |
| 2 | 81 | M | Suspicious cicatricial pemphigoid, MGD, Cch, trichiasis, lash loss, multiple glaucoma surgeries | No | Pain, tearing, burning for 4 years | 60%, all symptoms | 20/20 20/80 | Same | +++ | + |
| 3 | 55 | F | MGD, Cch, trichiasis | No | FBS, chronic irritation for 5 years | 100%, all symptoms | 20/20 20/20 | Same | + | − |
| 4 | 68 | M | Recurrent pterygium, trichiasis, lash | No | None | 80%, less weight in lids, more | 20/40 20/25 | 20/25 20/25 | − | − |

TABLE 4-continued

| Case | Age | Sex | Diagnosis | Allergy history | Complaints Before | Complaints After | Uncorrected Vision Before | Uncorrected Vision After | Conjunctival inflammation Before | Conjunctival inflammation After |
|---|---|---|---|---|---|---|---|---|---|---|
| | | | loss | | | opening, see better | | | | |
| 5 | 70 | M | MGD, lash loss, suspicious cicatricial pemphigoid, cornea epithelial defect | No | Persistent redness, blurry vision for 10 years, pain for 1 year | 100%, pain 70%, redness | 20/25 20/70 | 20/25 20/25 | +++ | − |
| 6 | 44 | M | MGD, LASIK dry eye | Pollen, mold, dust mite | Persistent redness, dryness, itching for 3 years | 75%, redness, dryness, 100%, itching | 20/20 20/20 | Same | ++ | + |
| 7 | 63 | F | MGD, Cch, conjunctivitis | NA | Dryness, itching for 5 years | 90%, all symptoms | 20/30 20/20 | Same | ++ | − |
| 8 | 60 | M | Conjunctivitis, trichiasis, punctuate keratopathy | NA | FBS, dryness, grittiness for 2 years | 100%, FBS, dryness 50%, grittiness | 20/50 20/40 | Same | ++ | + |
| 9 | 59 | M | MGD, conjunctivitis, | Pollen, mold, dust mite | Persistent redness, dryness for 8 years | 85%, all symptoms | 20/40 20/40 | Same | ++ | + |
| 10 | 42 | F | MGD, conjunctivitis | No | Pain, FBS for 10 days | 100%, all symptoms | 20/30 20/25 | 20/25 20/20 | − | − |
| 11 | 52 | M | Conjunctivitis, trichiasis | No | None | None | 20/25 20/25 | 20/20 20/20 | − | − |

MGD: Meibomian gland dysfunction;
Cch: Conjunctivochalasis;
FBS: Foreign body sensation;
LTD: Lipid tear deficiency;
NA: Not available;
Vision: upper line is for the right eye, lower line is for the left eye.

The clinical data support that ocular *demodex* infestation causes abnormalities in the ocular surface, lash follicles and meibomian glands.

One common manifestation of ocular *demodex* infestation is ocular surface inflammation. Eight of 11 patients showed conjunctival injection and among them 8 had an underlying disease that is known to be associated with conjunctival inflammation. To provide stronger evidence that ocular surface inflammation might be resulted from *demodex* infestation, changes were recorded after lid scrub with TTO. Lashes with CD were better and more effectively cleaned by lid scrub with 50% TTO than baby shampoo. After lid scrub with TTO, conjunctival inflammation was markedly reduced and the ocular surface and facial temperatures were also significantly reduced. In light of the fact that their prior inflammation was not controlled by anti-inflammatory medications in 8 cases and systemic immunosuppression in one case, we strongly suspect that *demodex*, if not causatively linked with, aggravates the existing inflammation.

Accompanied with the reduction of ocular surface inflammation was notable reduction of symptoms in 9 patients that presented with prior annoying irritation (Table 5). In addition to causing ocular surface inflammation, *demodex* might cause damage in the lash follicle as evidenced by the loss of lashes in 4 and intermittent trichiasis in 5 of 11 patients.

TABLE 5

Demodex Counts After Treatment.

| Case | CD at lashes | 0 week | 1 week | 2 week | 3 week | 4 week | 5 week | 6 week | 7 week | 8 week | 9 week |
|---|---|---|---|---|---|---|---|---|---|---|---|
| 1 | Diffuse | 26 | 12 | 5 | 3 | 0 | 11 | 8 | 2 | 4 | 2 |
| 2 | Diffuse | 16 | 2 | 4 | 8 | 3 | 4 | | | | |
| 3 | Sporadic | 5 | 1 | 0 | 0 | | | | | | |
| 4 | Diffuse | 13 | 3 | 3 | 1 | 0 | 0 | | | | |
| 5 | Sporadic | 6 | 1 | 2 | 0 | 0 | | | | | |
| 6 | Sporadic | 3 | 1 | 0 | 0 | | | | | | |
| 7 | Diffuse | 14 | 1 | 10 | 2 | 0 | 0 | | | | |
| 8 | Sporadic | 8 | 4 | 0 | 0 | | | | | | |
| 9 | Sporadic | 6 | 1 | 0 | 0 | | | | | | |

TABLE 5-continued

Demodex Counts After Treatment.

| Case | CD at lashes | 0 week | 1 week | 2 week | 3 week | 4 week | 5 week | 6 week | 7 week | 8 week | 9 week |
|---|---|---|---|---|---|---|---|---|---|---|---|
| 10 | Sporadic | 7 | 2 | 11 | 5 | 2 | 3 | 2 | | | |
| 11 | Diffuse | 16 | 7 | 0 | 0 | | | | | | |

Fourthly, *demodex* might cause damage in the meibomian gland leading to an abnormal lipid tear film as revealed by the kinetic analysis of tear interference images (Table 6).

TABLE 6

Kinetic Analysis of Tear Interference Images Before and After TTO Treatment

| Case | Lipid Pattern | | Lipid Spread Time | | Lipid Thickness | |
|---|---|---|---|---|---|---|
| | OD | OS | OD | OS | OD | OS |
| *Before TTO* | | | | | | |
| 1 | v | v | 1.93 | 2.32 | 70 | 60 |
| 2 | m | m | 2.12 | 1.73 | 100 | 70 |
| 3 | m | m | 2.7 | 1.54 | 50 | 60 |
| 4 | m | m | 1.74 | 3.09 | 90 | 70 |
| 5 | v | m | 1.74 | 1.54 | 70 | 50 |
| 6 | m | m | 1.93 | 1.54 | 80 | 60 |
| 7 | m | m | 2.31 | 2.31 | 60 | 70 |
| 8 | m | m | 1.73 | 1.54 | 80 | 50 |
| 9 | v | m | 1.93 | 1.93 | 80 | 60 |
| Mean | | | 2.01 | 1.95 | 75.6 | 61.1 |
| SD | | | 0.32 | 0.53 | 15.1 | 7.82 |
| *After TTO* | | | | | | |
| 1 | m | m | 1.37 | 1.73 | 90 | 80 |
| 2 | m | m | 1.16 | 1.35 | 80 | 70 |
| 3 | m | m | 1.16 | 0.97 | 60 | 60 |
| 4 | m | m | 1.54 | 1.35 | 70 | 80 |
| 5 | m | m | 0.77 | 1.16 | 70 | 60 |
| 6 | h | m | 1.16 | 1.16 | 80 | 80 |
| 7 | m | m | 1.16 | 2.31 | 40 | 40 |
| 8 | m | h | 1.35 | 1.35 | 70 | 60 |
| 9 | m | m | 1.16 | 1.35 | 80 | 70 |
| Mean | | | 1.20 | 1.41 | 71.1 | 66.7 |
| SD | | | 0.21 | 0.39 | 14.5 | 13.2 |
| T Test | | | 0.0003 | 0.012 | 0.38 | 0.30 |

Lipid pattern:
h: horizontal wavy;
v: vertically streaking;
m: mixed.

All 9 patients subjected to kinetic analyses of tear interference images showed Lipid Tear deficiency (LTD) dry eye. This finding supports the existence of meibomian gland dysfunction, presumably caused by either CD and debris from *demodex* that might have destabilized the lipid tear film or interfered with the meibum lipid formation.

Because TTO treatment led to a significant improvement in the spread time in the lipid tear film, resulting in an overall much more stable and even tear film, resolution of corneal epithelial abnormalities in some cases, and an improved visual acuity in others (Table 6), TTO lid scrub may have dissolved the keratinized plug in the meibomian gland orifice and facilitated the lipid expression. Furthermore, TTO lid scrub stimulates *demodex* to move out and might kill most, if not all, of *demodex* inside meibomian gland, and improve its function. Cleansing of *demodex* might also alter bacterial flora and load, which indirectly may also improve symptoms, inflammation or meibum lipid composition. Confirmation of *demodex*'s pathogenicity relies on a treatment with an agent such as TTO that can eradicate *demodex*.

Following are nine clinical examples (Cases 1 through 9).

CLINICAL EXAMPLES

Case Example No. 1

A 68 year-old female complained of foreign body sensation, redness and itching in the left eye for 2 years. On Feb. 4, 2004, she received surgery to remove primary pterygium and reconstruction with amniotic membrane transplantation. The pterygium recurred on May 4, 2004, and she received another pterygium removal and reconstruction with conjunctival autograft from the right eye. Nevertheless, the pterygium recurred shortly afterwards, and she was referred to Ocular Surface Center for being considered for re-operation for her multi-recurrent pterygium (FIG. 6A). On Jul. 7, 2004, besides recurrent pterygium, she was found to have meibomian gland dysfunction, conjunctivochalasis, and aqueous tear and lipid tear deficiency dry eye. Furthermore, her lashes were loaded with diffuse cylindrical dandruff (CD) (FIG. 6B). The diagnosis of ocular demodicosis was made because of a high *demodex* count of 19 per 8 lashes (i.e., 19 *demodex* mites found in a total of 8 lashes in two eyes). Lid hygiene, i.e., lid scrub with shampoo, was advised, but she did not notice any improvement 3 weeks later (Jul. 28, 2004). Therefore, non-preserved 0.2% dexamethasone was prescribed three times a day, both eyes, for 1 week with tapering for another week. She returned on Oct. 13, 2004 with less redness but her lashes were still coated with CD with a *demodex* count of 19. Therefore, her lid margins were coated with 50% Tea Tree Oil (TTO) for one time without lid scrub on Oct. 13, 2004. On Oct. 18, 2004, her lashes still presented with similar CD and the *demodex* count was 26. The above data indicated that both baby shampoo lid scrub and coating the lashes with 50% TTO could not eradicate ocular *demodex*. Because we subsequently found out that although 50% TTO can kill *demodex* in 14.8±9.5 min in vitro, it can stimulate *demodex* to move out of the lashes in vivo {described in separated paper}, we started office lid scrub recipe as described above on this patient on this visit. One week later she present with sporadic CD with the *demodex* count dropping to 12. Her symptoms decreased and her eyes could open with more comfort. Four weeks later, the *demodex* count dropped to 0, but rebounded to 11. Since then we had continued the same weakly office scrub and daily home scrub for a total of 9 weeks during which time the *demodex* counts rebounded 2 times and the final *demodex* count was 2. At the final visit, she presented with clean lashes (FIG. 6D), her conjunctiva was less red, and her symptoms improved 80% to the extent that her daily life was not disturbed. Interestingly, her inflamed recurrent pterygium became non-inflamed (FIG. 6C) to the point that no surgery was contemplated. Before treatment, the kinetic analysis of tear interference images by DR-1 showed a vertical pattern in both eyes, the lipid spread time of 1.93 sec and 2.32 sec, and the lipid thickness of 70 nm and 60 nm in the right eye and left eye. Respectively. After treatment, the lipid spread time was shortened to 1.37 sec and 1.73 sec and the lipid thickness was 90 nm and 80 nm in right eye and left eye, respectively.

The method and apparatus for kinetic analysis of tear interference images by DR-1 is described in detail in U.S. patent application Ser. No. 10/131,665 by Tseng and Goto, the teachings of which are incorporated herein by reference in their entirety.

FIG. 6 shows conjunctiva and lashes changes before and after TTO treatment. Before treatment, the conjunctiva and recurrent pterygium were red and elevated (6A), and the eye lashes showed diffuse CD (6B). After treatment, the conjunctiva was less inflamed (6C) and the eyelashes were clean (6D).

Case Example No. 2

Figure 7A:
FIG. 7A and FIG. 7B are photographs showing conjunctiva inflamed in both eyes wherein lashes had diffuse CD and high *demodex* count.
Figure 7B:
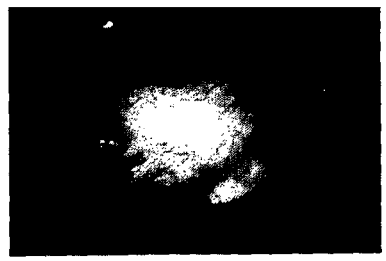
Figure 7C:
FIG. 7C and FIG. 7D show conjunctiva less inflamed in both eyes after TTO treatment.
Figure 7D:
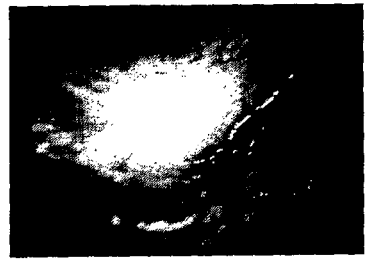
Figure 7E:
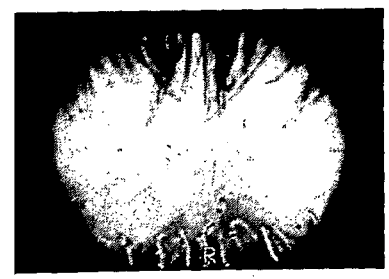
FIGS. 7E and 7F are images produced by kinetic analysis of tear interference before TTO treatment, images showing persistent cracking stripes in both eyes with uneven lipid tear film.
Figure 7F:
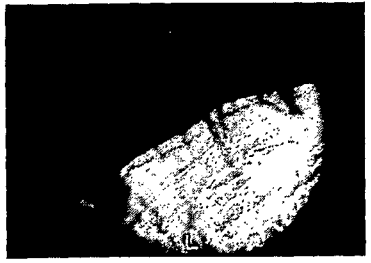
Figure 7G:
FIGS. 7G and 7H are images obtained after TTO treatment, the images showing that cracking stripes have disappeared and lipid film is more evenly distributed.
Figure 7H:
Figure 8A:
FIG. 8A through FIG. 8D is a set of photographs showing DR-1 changes before and after treatment.
Figure 8B:
Figure 8C:
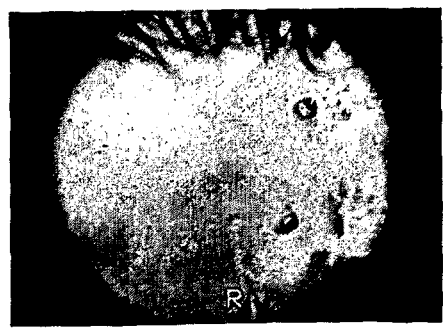
Figure 8D:
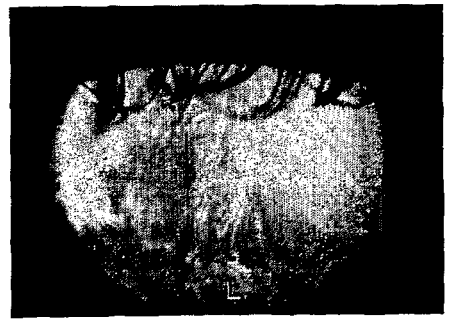
Figure 9A:
FIG. 9A through FIG. 9F are photographs showing conjunctiva, cornea and DR-1 in the Left Eye before and after TTO Treatment.
Figure 9B:
Figure 9C:
Figure 9D:
Figure 9E:
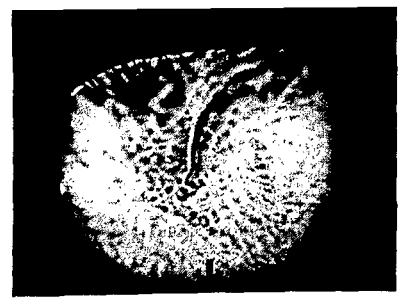
Figure 9F:

An 81 year-old male complained of dryness in the left eye worse than the right eye and chronic irritation for the past 4 years. His left eye received 6 times of glaucoma drainage implant surgeries for primary open angle glaucoma. On Nov. 11, 2002, he was referred to Ocular Surface Center and was found to have exposure keratopathy due to ectropion, misdirected lashes, cicatricial keratoconjunctivitis (thought to be due to old trachoma), meibomian gland dysfunction with lipid tear deficient (LTD) dry eye, and delayed tear clearance in both eyes. His conjunctiva was inflamed. His left eye was treated with non-preserved 1% methylprednisolone drops, and then with symblepharonlysis, fornix reconstruction, intraoperative application of mitomycin C, and amniotic membrane transplantation on Jan. 17, 2003. He also received subconjunctival injection of long-acting steroid (Keralog®) in the left eye on Jan. 7, 2003 and horizontal lid tightening of both lower lids on May 15, 2003 for ectropion. Despite all these procedures, he continued to complain of dryness, tearing, burning and fluctuating blurry vision. On Nov. 10, 2004, his conjunctiva was inflamed in both eyes (FIGS. 7A and 7B). His lashes had diffuse CD and the *demodex* count was 16. All the ocular medications were stopped. He received office TTO lid scrub and home lid scrub. Lashes became clean, and *demodex* count was 2, 4, 8, 3, 4 at the ensuring weekly follow up visit. His conjunctiva became less inflamed in both eyes (FIGS. 7C and 7D), his symptoms were 60% relieved, and his vision improved 1 line in the right eye and 2 lines in the left eye. The kinetic analysis of tear interference images by DR-1 showed a mixed pattern in both eyes before and after treatment. The lipid spread time was 2.12 and 1.73 sec before and 1.16 and 1.35 sec after treatment, lipid thickness was 100 nm and 70 nm before, and 80 and 70 nm after treatment in right eye and left eye, respectively. Before treatment, DR-1 showed persistent cracking stripes at the inferior cornea in both eyes with uneven lipid tear film (FIGS. 7E and 7F). After treatment, the cracking stripes disappeared and the lipid film became more evenly distributed (FIGS. 7G and 7H).

FIG. 7 shows conjunctiva and DR-1 changes before and after TTO treatment. Both bulbar and tarsal conjunctivae were red in the right eye (7A) and the left eye (7B) before TTO treatment. They became less inflamed after TTO treatment (7C, and 7D, respectively). DR-1 showed an uneven distribution of the lipid tear film and persistent cracking stripes on the inferior cornea of the right eye (7E) and the left eye (7F). These changes disappeared and the lipid film became more evenly distributed after treatment (7G and 7H).

Case Example No. 3

A 55 year-old female complained of foreign body sensation and irritation in the left eye worse than the right eye for 5 years. She received bilateral upper lid blepharoplasty in 1998, and surgical excision of conjunctival cysts for 3 times, epilation of trichiasis, and insertion of punctual plugs in 2002. Because of persistent foreign body sensation and chronic irritation, she was referred to Ocular Surface Center and found on Jul. 17, 2002 to have trichiasis (2 on the left upper lid), meibomian gland dysfunction, and lipid tear deficient dry eye. She received 0.2% non-preserved dexamethasone eye drops, epilation, subconjunctival injection of long-acting steroid (KERALOG®). On Aug. 12, 2004, she received excision of conjunctivochalasis and reconstruction with amniotic membrane transplantation in the left eye, and wore a bandage contact lens postoperatively. Despite these treatments, she continued to complain of these symptoms. On Nov. 15, 2004, her lashes were found to have sporadic CD, and the *demodex* count was 5. She received lid scrub with 50% TTO and home lid scrub with TT shampoo. The *demodex* count dropped to 1 on Nov. 22, 2004, and 0 on Nov. 29, 2004, and her lashes were free of CD. During the ensuing one month, the *demodex* count remained 0 without rebound. One surprising founding was that trichiasis did not recur during the two months of follow up. Her eyes could open more comfortable without any foreign body sensation and irritation. The DR-1 pattern was mixed in both eyes before and after treatment. The lipid spread time dropped from 2.7 sec and 1.54 sec to 1.16 sec and 0.97 sec in the right eye and the left eye, respectively after treatment. The lipid thickness was 50 nm and 60 nm before and 60 nm and 60 nm in right eye and left eye, respectively.

Case Example No. 4

This 68 year-old male presented to Ocular Surface Center on Oct. 7, 2002 for the management of primary pterygium in his right eye. Interestingly, he had been suffering from misdirected lashes due to an unknown cause in the left eye worse than the right eye for more than 20 years, to which he received weekly epilation by his wife. He received removal of pterygium and reconstruction with amniotic membrane transplantation on Feb. 13, 2003. Although he felt fine after surgery, conjunctival redness persisted and became more obvious on Jun. 2, 2003, i.e., 4 months after surgery. He also complained of foreign body sensation and itching. Nine months after surgery, recurrent pterygium was noted and surgery was performed on Jan. 9, 2004 with intraoperative application of mitomycin C and reconstruction with amniotic membrane transplantation. After the second surgery he felt some foreign body sensation, which disappeared 4 months after surgery. He returned for a routine check up on Dec. 1, 2004 without obvious discomfort, but her lashes had diffuse CD, right eye worse than left eye. The *demodex* count was 13. He received the treatment on Dec. 1, 2004. One week later, he felt "less weight" in the eyelid, could see better, and noted that he was less bothered by misdirected lashes. In the following week, he declared that it required epilated every 5 days in the past, but now felt fine without it for more than 14 days after epilation. The *demodex* count dropped to 3, 3, 1, and 0 in the ensuing weekly follow up after treatment. Her vision improved one line in the right eye and 4 lines in the left eye. Before treatment, DR-1 showed that the lipid tear film was colorful, unevenly distributed with numerous granules in the right eye and a persistent cracking patches in the inferior cornea of the left eye. After treatment, DR-1 showed a more evenly distributed lipid film without granules or cracking patches. The lipid spread time was shortened in both eyes despite the fact that the lipid tear film thickness decreased in the right eye.

FIG. 8A through 8D is a set of photographs showing DR-1 changes before and after treatment. Before treatment, the lipid film was colorful and unevenly distributed with many granules in the right eye (8A) and persistent cracking patch predominantly at the inferior cornea in the left eye (8B). After treatment the lipid film became more evenly distributed with less granules (8C) and did not have any cracking patches in the left eye (8D).

Case Example No. 5

This 70 year old optometrist complained of persistent redness and blurry vision in the left eye and misdirected lashes in both eyes for more than 10 years. He was initially diagnosed ocular cicatricial pemphigoid and was treated with Dapsone and topical Lotemax in 2001 without relief. His conjunctival redness was worse in the morning upon awakening. He was first seen at Ocular Surface Center on Jun. 16, 2003 to have cicatricial keratoconjunctivitis, conjunctivochalasis, trichiasis, meibomian gland dysfunction, floppy eye lids, and delayed tear clearance. He was asked to stop Lotemax and Dapsone and started with oral Cyclophosphamide 50 mg tid. However, his symptoms didn't diminish even though he subsequently received multiple epilation, Restasis, 0.2% non-preserved dexamethosone, artificial tears, and subconjunctival injection of KERALOG at different visits. He received symblepharon lysis, removal of conjunctivochalasis, intraoperative application of mitomycin, and reconstruction with amniotic membrane in the right eye on Dec. 19, 2003, and the same procedure on Jan. 23, 2004 in the left eye. Although these procedures made him feel better for several months, conjunctival redness persisted and ocular irritation returned 4 months later. On Aug. 2, 2004, he was noted to have superficial corneal erosion with pain and irritation in the left eye. Although soft contact lens made him feel free of pain and irritation, the corneal lesion persisted. He was inserted with a punctal plug in the left lower lid on Aug. 2, 2004 for aqueous tear deficient dry eye, but did not notice improvement. On Dec. 15, 2004, his lashes were noted to have CD and the *demodex* count was 6. Thus he began office scrub with TTO and home scrub with TTO shampoo, and his topical medication was limited to artificial tears only. Surprisingly, on the next visit his eye irritation was relieved, redness decreased and his vision improved from 20/70 to 20/25. Although he lost his contact lens after the first TTO treatment, he did not note any pain in the left eye. The *demodex* count dropped to 0 after 2 weeks of treatment without recurrence.

Before the treatment, there was redness on the forehead, cheeks, nose, chin and eyelid, which was dramatically decreased after treatment, it was conformed by the infrared picture. From FIG. 9. we can see infrared picture, conjunctiva injection, cornea lesion and DR-1 at left eye dramatically changed at the time initiated the treatment and the time *demodex* dropped to 0.

Infrared thermographs show changes in the Left Eye before and after TTO Treatment. Infrared thermographs (not presented here to preserve patient confidentiality) show diffuse redness on the whole face including the upper and lower lids before treatment, and less redness after treatment. FIGS. 9A through 9F are photographs showing conjunctiva, cornea and DR-1 in the Left Eye before and after TTO Treatment. The bulbar conjunctiva was red before treatment (9A), and was less red after treatment (9B). The cornea showed an irregular epithelium before treatment (9C), which disappeared after treatment (9D). DR-1 showed that the lipid film was colorful, uneven and had cracking stripes around the corneal lesion before treatment (9E), but became more even and free of these cracking stripes after treatment (9F).

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating an ocular *Demodex* infestation or *Demodex*-induced blepharitis in an individual in need thereof, comprising administering to the individual a therapeutically-effective amount of a composition consisting essentially of terpinen-4-ol as an active agent and at least one pharmaceutically-acceptable excipient.

2. The method of claim 1, comprising administering the composition topically.

3. The method of claim 1, comprising administering the composition to the eyelid margin and eyelash.

4. The method of claim 1, further comprising scrubbing the eyelid margin and eyelash roots with the composition.

5. The method of claim 1, wherein the composition is a shampoo, gel, solution or suspension.

6. The method of claim 1, wherein the pharmaceutically-acceptable excipient is selected from water, saline, a lubricant, dextrose, ethanol, or any combination thereof.

7. The method of claim 6, wherein the pharmaceutically-acceptable excipient is selected from corn oil, olive oil, glycerol, and petroleum jelly.

8. The method of claim 1, comprising administering the composition weekly for at least 4 weeks.

9. The method of claim 1, comprising administering a first dose of the composition weekly and a second dose of the composition daily.

10. The method of claim 1, comprising administering the composition twice daily for one month, then administering the composition daily.

11. The method of claim 1, comprising administering the composition for at least 3 minutes, for at least 4 minutes, for at least 5 minutes, for at least 10 minutes, or for at least 15 minutes.

12. The method of claim 1, wherein the individual is refractory to an anti-inflammatory, conventionally anti-microbial antibiotic, or an anti-allergy therapy for ocular *Demodex* infestation or *Demodex*-induced blepharitis.

* * * * *